United States Patent
Simard et al.

(10) Patent No.: US 7,790,924 B2
(45) Date of Patent: Sep. 7, 2010

(54) PROCESS FOR PREPARING ALKYLENE OXIDE-ADDUCTED HYDROCARBYL AMIDES

(75) Inventors: Francois Simard, Novato, CA (US); Richard E. Cherpeck, Cotati, CA (US)

(73) Assignee: Chevron Oronite Company LLC, San Ramon, CA (US)

( * ) Notice: Subject to any disclaimer, the term of this patent is extended or adjusted under 35 U.S.C. 154(b) by 1332 days.

(21) Appl. No.: 10/993,344

(22) Filed: Nov. 19, 2004

(65) Prior Publication Data

US 2006/0107584 A1    May 25, 2006

(51) Int. Cl.
*C07C 231/02* (2006.01)
(52) U.S. Cl. .................. 564/135; 554/35; 554/61; 554/68; 564/136; 564/137; 564/141; 564/215; 564/224
(58) Field of Classification Search ............... 564/135, 564/136, 137, 141, 215, 224; 554/35, 61, 554/68
See application file for complete search history.

(56) References Cited

U.S. PATENT DOCUMENTS

| 4,297,107 | A | 10/1981 | Boehmke |
|---|---|---|---|
| 4,729,769 | A | 3/1988 | Schlicht et al. |
| 6,034,257 | A | 3/2000 | Oftring et al. |
| 6,312,481 | B1 | 11/2001 | Lin et al. |

FOREIGN PATENT DOCUMENTS

| EP | 0488747 | 6/1992 |
|---|---|---|
| EP | 1431374 | 6/2004 |
| EP | 1435385 | 7/2004 |
| EP | 1435386 | 7/2004 |
| WO | WO 2005/023965 | 3/2005 |

*Primary Examiner*—Shailendra Kumar

(57) ABSTRACT

A process is described for preparing alkylene oxide-adducted hydrocarbyl amides having less than 2 wt % of amine by-products by a) reacting a $C_4$-$C_{30}$ fatty acid or fatty acid lower alkyl ester with a mono- or di-hydroxy hydrocarbyl amine to form a hydrocarbyl amide;

b) reacting the hydrocarbyl amide with alkylene oxide; and c) extracting the product of b) with water, acidic water, or water-containing inorganic salts or a combination thereof at a temperature from about 5° C. to 95° C. to yield an alkylene oxide-adducted hydrocarbyl amide having less than 2 wt % of amine by-products.

26 Claims, No Drawings

PROCESS FOR PREPARING ALKYLENE OXIDE-ADDUCTED HYDROCARBYL AMIDES

This invention relates to a process for preparing alkylene oxide-adducted hydrocarbyl amides. More particularly, this invention involves a process for reducing amine by-products from the process of preparing alkylene oxide-adducted hydrocarbyl amides to less than 2 wt % amine by-products.

BACKGROUND OF THE INVENTION

Alkylene oxide-adducted hydrocarbyl amides have efficacious detergency properties. Their usefulness in hydrocarbon fuels, e.g. fuels in the gasoline or diesel boiling range, is well known for preventing deposits in internal combustion engines, controlling octane requirement increases and reducing octane requirement. The driveability of vehicles is believed to be enhanced when using fuels containing alkylene oxide-adducted hydrocarbyl amides.

U.S. Pat. No. 4,297,107 to Boehmke, issued on Oct. 27, 1981, discloses a fuel comprising a hydrocarbon water and emulsifier wherein the emulsifier is a non-ionic emulsifier and comprises the addition product of ethylene oxide or propylene oxide and a carboxylic acid amide with 9 to 21 carbon atoms.

U.S. Pat. No. 6,312,481 to Lin et al., issued on Nov. 6, 2001, discloses the use of monoamide-containing polyether alcohol compounds as additives in fuel compositions and the use of these compounds to decrease intake valve deposits, control octane requirement increase, and reduce octane requirement.

The preparation of alkylene oxide-adducted hydrocarbyl amides may be made by any method familiar to one skilled in the art. For example, one may begin by reacting a fatty acid ester with a mono- or di-hydroxy hydrocarbyl amine to first yield a hydroxylated fatty acid amide as an intermediate reaction product. The alkylene oxide-adducted hydrocarbyl amide can then be obtained by further reaction of the intermediate with an alkylene oxide, such as ethylene oxide or propylene oxide. However, during the course of the reaction, low molecular weight by-products, particularly amine by-products, e.g. alkoxylated amines, such as propoxylated diethanolamines, are produced that are counter benefit to the properties of the alkylene oxide-adducted hydrocarbyl amide. Such amine by-products are polar, basic and water soluble, resulting in the tendency to accumulate in the water bottoms of fuel storage tanks and on metal surfaces. Fuel tank water bottoms are notorious for harboring numerous accumulated compounds. Under the right conditions, certain low molecular weight amines may react with certain other compounds present, e.g. acidic corrosion inhibitors, possibly forming salts or gums which could potentially form deposits within the distribution system, e.g. filters, flow meters, etc. Within an internal combustion engine, there may be interactions between the amine by-products and other additive components in fuel compositions that could aggravate engine performance due to increased engine wear or sludge or varnish accumulation. Removal of amine by-products resulting from the preparation of alkylene oxide-adducted hydrocarbyl amides is complicated because of the propensity of these materials to form emulsions with aqueous extractions. Thus, it is highly desirable to minimize amine by-products from additive packages containing alkylene oxide-adducted hydrocarbyl amides.

SUMMARY OF THE INVENTION

The present invention relates to a process for preparing alkylene oxide-adducted hydrocarbyl amides. More particularly, this invention involves a process for reducing amine by-products, particularly alkoxylated amines such as propoxylated diethanolamines, from the process of preparing alkylene oxide-adducted hydrocarbyl amides to less than 2 wt % amine by-products.

The present process comprises:
a) reacting a $C_4$-$C_{30}$ fatty acid or fatty acid lower alkyl ester with a mono- or di-hydroxy hydrocarbyl amine to form a hydrocarbyl amide;
b) reacting the hydrocarbyl amide with alkylene oxide; and
c) extracting the product of b) with water, acidic water, or water-containing inorganic salts, or a combination thereof at a temperature from about 5° C. to 95° C. to yield an alkylene oxide-adducted hydrocarbyl amide having less than 2 wt %, preferably less than 1.5 wt %, more preferably less than 1.0 wt %, of amine by-products.

In a further embodiment, the present invention is directed to alkylene oxide-adducted hydrocarbyl amides having less than 2 wt % of amine by-products produced by the process of the present invention.

Among other factors, the present invention is based on the discovery that amine by-products, e.g. alkoxylated amines such as propoxylated diethanolamines, from the preparation of alkylene oxide-adducted hydrocarbyl amides can be effectively reduced to less than 2 wt % amine by-products by employing the unique process described herein. The removal of such amine by-products minimizes potential fuel distribution system interactions as well as enhances the driveability of vehicles utilizing alkylene oxide-adducted hydrocarbyl amides as fuel additives in gasoline or diesel fuels.

DETAILED DESCRIPTION OF THE INVENTION

As stated above, the present invention relates to a process for preparing alkylene oxide-adducted hydrocarbyl amides. More particularly, this invention relates to a process for reducing alkoxylated amines, particularly alkoxylated amines such as propoxylated diethanolamines, from the process of preparing alkylene oxide-adducted hydrocarbyl amides to less than 2 wt % amine by-products.

Prior to discussing the present invention in detail, the following terms will have the following meanings unless expressly stated to the contrary.

Definitions

The term "amino" refers to the group: —$NH_2$.

The term "hydrocarbyl" refers to an organic radical primarily composed of carbon and hydrogen which may be aliphatic, alicyclic, aromatic or combinations thereof, e.g., aralkyl or alkaryl. Such hydrocarbyl groups may also contain aliphatic unsaturation, i.e., olefinic or acetylenic unsaturation, and may contain minor amounts of heteroatoms, such as oxygen or nitrogen, or halogens, such as chlorine. When used in conjunction with carboxylic fatty acids, hydrocarbyl will also include olefinic unsaturation.

The term "alkyl" refers to both straight- and branched-chain alkyl groups.

The term "lower alkyl" refers to alkyl groups having 1 to about 6 carbon atoms and includes primary, secondary and tertiary alkyl groups. Typical lower alkyl groups include, for example, methyl, ethyl, n-propyl, isopropyl, n-butyl, sec-butyl, t-butyl, n-pentyl, n-hexyl and the like.

The term "alkenyl" refers to an alkyl group with unsaturation.

The term "alkylene oxide" refers to a compound having the formula:

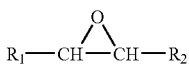

wherein $R_1$ and $R_2$ are each independently hydrogen or lower alkyl having from 1 to about 6 carbon atoms.

The Process

The process for the preparation of the alkylene oxide-adducted hydrocarbyl amides of the present invention will now be described hereinbelow.

The first step of the present invention involves preparing a hydrocarbyl amide having the following structure:

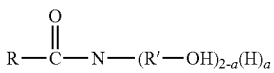

wherein,
R is a hydrocarbyl group having from about 3 to 29, preferably from about 5 to 23, more preferably from about 5 to 19, carbon atoms;
R' is a divalent alkylene group having from about 1 to 10, preferably from about 2 to 5, more preferably from about 2 to 3, carbon atoms; and
a is an integer from 0 to 2. Preferably, a is 0.

The hydrocarbyl amide is typically the reaction product of a fatty acid or fatty acid lower alkyl ester and ammonia or a mono- or di-hydroxy hydrocarbyl amine.

Preferably, the hydrocarbyl group, R, is alkyl or alkenyl, more preferably, alkyl.

The acid moiety of the fatty acid or fatty acid lower alkyl ester may preferably be RCO— wherein R is as defined above and is typified by caprylic, caproic, capric, lauric, myristic, palmitic, stearic, oleic, linoleic, etc. Preferably the acid is saturated although unsaturated acid may be present.

Preferably, the reactant bearing the acid moiety may be natural oil: coconut, babassu, palm kernel, palm, olive, castor, peanut, rape, beef tallow, lard, lard oil, whale blubber, sunflower, etc. Typically the oils which may be employed will contain several acid moieties, the number and type varying with the source of the oil.

The lower alkyl group of the fatty acid lower alkyl ester may be derived from a lower alkyl ester of a fatty acid. Preferred lower alkyl esters will have a lower alkyl group having from about 1 to 6, more preferably from about 1 to 4, most preferably from about 1 to 2, carbon atoms, e.g., methyl ester, ethyl ester, propyl ester, isopropyl ester, butyl ester, isobutyl ester, pentyl ester, isopentyl ester, and hexyl ester. Preferably, the lower alkyl ester is a methyl ester.

The acid moiety may be supplied in a fully esterified compound or one which is less than fully esterified, e.g., glyceryl tri-stearate, glyceryl di-laurate, glyceryl mono-oleate, etc. Esters of polyols, including diols and polyalkylene glycols may be employed such as esters of mannitol, sorbitol, pentaerythritol, polyoxyethylene polyol, etc.

Ammonia or a mono- or di-hydroxy hydrocarbyl amine with a primary or secondary amine nitrogen may be reacted to form the hydrocarbyl amides of the present invention. Typically, the mono- or di-hydroxy hydrocarbyl amines may be characterized by the formula:

$$HN(R'OH)_{2-b}H_b$$

wherein R' is as defined above and b is 0 or 1.

Typical amines may include, but are not limited to, ethanolamine, diethanolamine, propanolamine, isopropanolamine, dipropanolamine, di-isopropanolamine, butanolamines etc. Preferably, the amine is selected from the group consisting of ethanolamine, diethanolamine, propanolamine and dipropanolamine. Diethanolamine is most preferred.

Reaction may typically be effected by maintaining the reactants at from about 100° C. to 200° C., preferably from about 120° C. to 155° C., more preferably from about 140° C. to 155° C. for 1 to about 10 hours, preferably about 4 hours. Reaction may be carried out in a solvent, preferably one which is compatible with the ultimate composition in which the product is to be used. A base catalyst, such as potassium or sodium methoxide, could also be used to speed the reaction, lower the reaction temperature and minimize side products, such as piperazine. The catalyst, if used, may be removed at the conclusion of the reaction by appropriated techniques known to the skilled artisan including neutralization/water extraction, neutralization/precipitation and filtration or a mixture of these two methods.

Typical reaction products which may be employed in the practice of this invention may include those formed from esters having the following acid moieties and alkanolamines:

TABLE 1

| Acid Moiety in Ester | Amine |
| --- | --- |
| Lauric Acid | Propanolamine |
| Lauric Acid | Diethanolamine |
| Lauric Acid | Ethanolamine |
| Lauric Acid | Dipropanolamine |
| Palmitic Acid | Diethanolamine |
| Palmitic Acid | Ethanolamine |
| Stearic Acid | Diethanolamine |
| Stearic Acid | Ethanolamine |

Other useful mixed reaction products with alkanolamines may be formed from the acid component of the following oils: coconut, babassu, palm kernel, palm, olive, castor, peanut, rape, beef tallow, lard, whale blubber, corn, tall, cottonseed, etc.

In one preferred aspect of this invention, the desired reaction product may be prepared by the reaction of (i) fatty acid lower alkyl ester and (ii) diethanolamine.

Typical fatty acid lower alkyl esters may include lower alkyl esters of the fatty acids wherein the lower alkyl group contains from about 1 to 6, preferably from about 1 to 4, more preferably from about 1 to 2, carbon atoms. Preferably, the lower alkyl ester is a methyl ester. These acids may be characterized by the formula RCOOH wherein R is an alkyl hydrocarbon group containing from about 7 to 15, preferably from about 11 to 13, more preferably about 11 carbon atoms.

Typical of the fatty acid lower alkyl esters which may be employed may be tri-laurate, tri-stearate, tri-palmitate, di-laurate, mono-stearate, di-laurate, tetra-stearate, tri-laurate, mono-palmitate, penta-stearate, mono-stearate.

The esters may include those wherein the acid moiety is a mixture as is typified by the following natural oils: coconut, babassu, palm kernel, palm, olive, caster, peanut, rape, beef tallow, lard (leaf), lard oil, whale blubber.

The preferred ester is coconut oil lower alkyl ester which contains the following acid moieties:

TABLE 2

| Fatty Acid | Moiety Wt. % |
|---|---|
| Caprylic | 8.0 |
| Capric | 7.0 |
| Lauric | 48.0 |
| Myristic | 17.5 |
| Palmitic | 8.2 |
| Stearic | 2.0 |
| Oleic | 6.0 |
| Linoleic | 2.5 |

Examples of desirable alkyl amides suitable for the present invention include, but are not limited to, octyl amide (capryl amide), nonyl amide, decyl amide (caprin amide), undecyl amide dodecyl amide (lauryl amide), tridecyl amide, teradecyl amide (myristyl amide), pentadecyl amide, hexadecyl amide (palmityl amide), heptadecyl amide, octadecyl amide (stearyl amide), nonadecyl amide, eicosyl amide (alkyl amide), or docosyl amide (behenyl amide). Examples of desirable alkenyl amides include, but are not limited to, palmitoolein amide, oleyl amide, isooleyl amide, elaidyl amide, linolyl amide, linoleyl amide. Preferably, the alkyl or alkenyl amide is a coconut oil fatty acid amide.

The preparation of hydrocarbyl amides from fatty acid esters and alkanolamines is described, for example, in U.S. Pat. No. 4,729,769 to Schlicht et al., the disclosure of which is incorporated herein by reference.

In the second step of the process, the intermediate, hydrocarbyl amide, produced in the first step is adducted with alkylene oxide. The alkylene oxide which is adducted to the hydrocarbyl amide is derived from an alkylene group having from about 2 to 5 carbon atoms. Preferably, the alkylene oxide is selected from the group consisting of ethylene oxide, propylene oxide, butylene oxide, and pentylene oxide. Ethylene oxide and propylene oxide are particularly preferred. In addition, mixtures of alkylene oxides are desirable in which, for example, a mixture of ethylene oxide and propylene oxide may be used to form the alkylene oxide-adducted hydrocarbyl amide of the present invention. A respective molar ratio of from about 1:5 to 5:1 may be used in the case of a mixture of ethylene oxide and propylene oxide.

A desirable number of moles of the alkylene oxide to be adducted to the hydrocarbyl amide will be in the range of from about 1 to 30 moles of alkylene oxide per 1 mole of hydrocarbyl amide. More preferably, the range of from about 2 to 20 moles is particularly desirable. Most preferably, the range of from about 2 to 10 moles is most preferable as a molar range of the alkylene oxide per mole of hydrocarbyl amide.

Preferably, the alkylene oxide-adducted hydrocarbyl amide is derived from an alkylene oxide-adduction reaction involving a coconut oil fatty acid amide with ethylene oxide and propylene oxide. However, the alkylene oxide adducted hydrocarbyl amides useful as fuel additives in the present invention can be also a mixed product wherein various types and different moles of alkylene oxide and can be adducted to various types of hydrocarbyl amides. Most preferably, the alkylene oxide-adducted hydrocarbyl amide is derived from an alkylene oxide-adduction reaction involving a coconut oil fatty acid amide with propylene oxide.

The final step in the process of the present invention involves reducing the amine by-products. In the course of the reactions described above, various amine by-products may be formed that may have an adverse affect on fuel distribution systems as discussed in the background above. These amine by-products may be in the form of diethanolamine or alkoxylated diethanolamine or mixtures thereof. A particular concern is propoxylated diethanolamine. The amine-by-products may be effectively removed by extraction with water, acidic water, or water-containing inorganic salts or a combination thereof. Preferably, the inorganic salts of the water-containing inorganic salts may be derivations of sodium, lithium, potassium, bromine, chlorine, iodine, acetate, ammonium and sulfate; more preferably, sodium, potassium, chlorine, ammonium, and sulfate; and most preferably, sodium chloride. This extraction procedure is more effective than using filtration through acidic solid supports such as acidic alumina, silica gel, or magnesium silicate (Florisil®, Magnesol®). Preferably, the process of the present invention will utilize extraction with water, water containing inorganic salts, or a combination thereof. The effectiveness of the extraction is influenced by the number of washes, quantity of extractants, i.e., water or water containing inorganic salts, used with each wash, temperature, length of extraction, etc. Typically, the alkylene oxide-adducted hydrocarbyl amide would be extracted with a water/sodium chloride solution at a temperature ranging from about 5° C. to 95° C., preferably from about 5° C. to 50° C., more preferably from about 5° C. to 30° C. for a time ranging from about 10 to 120 minutes. The final alkylene oxide-adducted hydrocarbyl amide obtained after this extraction step will typically have less than 2 wt %, preferably less than 1.5 wt %, more preferably less than 1.0 wt %, of amine by-products, particularly alkoxylated amines such as propoxylated diethanolamines.

The Alkylene Oxide-Adducted Hydrocarbyl Amide

The present invention further relates to an alkylene oxide-adducted hydrocarbyl amide having less than 2 wt % of amine by-products as described above prepared by the process of the present invention, having from about 1 to 30 moles, preferably from about 2 to 20 moles, more preferably from about 2 to 10 moles, of alkylene oxide per mole of hydrocarbyl amide. The alkylene oxide-adducted hydrocarbyl amide having less than 2 wt % of amine by-products will have the following structure:

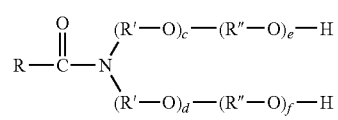

wherein,
R is a hydrocarbyl group having from about 3 to 29, preferably from about 5 to 23, more preferably from about 5 to 19, carbon atoms;
R' is a divalent alkylene group having from about 1 to 10, preferably from about 2 to 5, more preferably from about 2 to 3, carbon atoms;
R" is a divalent alkylene group having from about 2 to 5, preferably from about 2 to 3, carbon atoms;
c and d are independently 0 or 1, preferably both are 1; and e and f are independently integers from about 0 to 20, such that the total of e plus f ranges from about 1 to 40.

Preferably, the hydrocarbyl group, R, is alkyl or alkenyl, more preferably, alkyl. Preferably, e and f are independently integers from about 0 to 15, such that the total of e plus f ranges from about 1 to 30. More preferably, e and f are independently integers from about 0 to 10, and that the total of e plus f ranges from about 1 to 20.

EXAMPLES

The invention will be further illustrated by the following examples, which set forth particularly advantageous method embodiments. While the Examples are provided to illustrate the present invention, they are not intended to limit it.

Example 1

The following example illustrates a typical process for preparing the alkylene oxide-adducted hydrocarbyl amides of the present invention having less than 2 wt % amine by-products.

1a. Preparation of Cocoamide-DEA

To a flask equipped with a mechanical stirrer and thermometer was added 2000 grams (g) of methyl cocoate, i.e. methyl ester of coconut oil, with less than 0.05 wt % glycerol. Then 926 g of diethanolamine (DEA) was added. The mixture was heated to about 150° C. for about 4 hours. At the end of the reaction time, the mixture is cooled to about 95° C. and stripped under vacuum at about 450 mm Hg to remove methanol. The DEA content of the product was less than 2.0 wt %.

1b. Preparation of Propoxylated Cocoamide-DEA

In a typical preparation of propoxylated cocamide-DEA, 2000 g of cocoamide-DEA from Example 1a is charged to an autoclave equipped with stirrer and hot oil cooling jacket. Then 37 g of potassium hydroxide is added. The autoclave is heated to about 120° C. and vacuum of less than 30 mm Hg is applied to remove the water formed. After bringing the autoclave to atmospheric pressure with nitrogen, 1548 g of propylene oxide is added over about 4 hours. The reaction is completed about 6 hours after the propylene oxide is finished charging. The autoclave is cooled to about 95° C. and the catalyst is removed by treating with Florisil, water and filter aid. The mixture is filtered on a Buchner funnel. The product will typically contain from about 2 to 25 wt % propoxylated-DEA (PO-DEA) when determined by gas chromatography.

Example 2

2 Washes with Water/NaCl, Toluene, 80° C.

To a flask equipped with a mechanical stirrer and thermometer was added 200 g of propoxylated cocoamide-DEA prepared in a manner similar to the procedure described in Example 1 and having a PO-DEA content of about 23.2 wt % and 110 g of toluene. To the mixture was added 200 g of water at about 80° C. and 26.8 g of saturated sodium chloride solution. After mixing for 30 minutes at about 80° C., the mixing was stopped. The phases were allowed to separate for 30 minutes. The bottom aqueous phase was removed. The organic phase was washed with water and saturated sodium chloride one more time and phases separated. The second aqueous phase was removed and combined with the first aqueous phase. The organic phase was rotary evaporated at about 95-100° C. under vacuum of <30 mm Hg for 30 minutes or until all of the toluene and water in the organic phase was removed. The stripped product was weighed and analyzed. The water soluble fraction into the aqueous phase was also extracted with ethyl acetate using a liquid/liquid extraction apparatus. The PO-DEA content was effectively reduced from about 23.2 wt % to about 1.6 wt % as determined by gas chromatography.

Example 3

2 Washes with Water/NaCl, 20-30° C., No Solvent

To a flask equipped with a mechanical stirrer and thermometer was added 200 g of propoxylated cocoamide-DEA preferred in a manner similar to the procedure described in Example 1 and having a PO-DEA content of about 23.2 wt %, 200 g of water and 26.8 g of saturated sodium chloride solution. After mixing for 30 minutes at 20-30° C., the mixing was stopped. The phases were allowed to separate 30 minutes. The bottom aqueous phase was removed. The top organic layer was washed with water and saturated sodium chloride one more time and phase separated. The organic phase was rotary evaporated at about 95-100° C. under vacuum of <30 mm Hg for 30 minutes. The stripped product was weighed and analyzed by gas chromatography. The PO-DEA content was effectively reduced from about 23.2 wt % to about 1.4 wt %.

Example 4

Lower PO-DEA Content, No NaCl, with Solvent)

The procedure of Example 4 was performed as described in Example 2 except no NaCl was used. Propoxylated cocoamide-DEA with 2.8 wt % PO-DEA was water washed. However, the water washing was done with solvent but without NaCl. The PO-DEA content was effectively reduced from 2.8 wt % to 1.0 wt %.

Example 5

Lower PO-DEA Content, No NaCl, No Solvent

The procedure of Example 5 was performed as described in Example 2 but with no solvent and no NaCl. The PO-DEA content was effectively reduced from 2.8 wt % to 0.9 wt %.

Comparative Example A

Removal with Magnesium Silicate

To a flask equipped with a mechanical stirrer and thermometer was added 100 grams of propoxylated cocoamide-DEA having a PO-DEA content of about 2.8 wt %, 15 g of magnesium silicate (Dallas Company Magnesol HMR-LS), 1.5 g of filter-aid (Celite 503) and 5 g of water. After mixing for 2 hours at 95° C., the mixing was stopped and the product was filtered and analyzed by gas chromatography. The PO-DEA content was only reduced to 2.3 wt %.

Comparative Example B

Removal with Magnesium Silicate without Water

Comparative Example A was repeated with no water addition. The PO-DEA content was reduced to 2.0 wt %.

Comparative Example C

Removal with Magnesium Silicate at Lower Temperature and without Water

Comparative Example A was repeated with no water addition and at 50° C. The PO-DEA content was reduced to 2.2 wt %.

Comparative Example D

Removal with Silica Gel

To a flask equipped with a mechanical stirrer and thermometer was added 75 g of propoxylated cocoamide-DEA having a PO-DEA content of about 2.8 wt %, 11.3 g of silica gel and 3.8 g of water. After mixing for 2 hours at 95° C., the mixing was stopped and the product was filtered and analyzed by gas chromatography. The PO-DEA content was only reduced to 2.1 wt %.

Comparative E

Removal with Silica Gel at Lower Temperature

Comparative Example D was repeated at 50° C. The PO-DEA content was reduced to 2.5 wt %.

Comparative F

Removal with Silica Gel at Lower Temperature and without Water

Comparative Example D was repeated at 50° C. and without water. The PO-DEA content was reduced to 2.2 wt %.

Comparative Example G

Removal with Acidic Alumina

To a flask equipped with a mechanical stirrer and thermometer was added 75 g of propoxylated cocoamide-DEA having a PO-DEA content of about 2.8 wt % and 11.3 g of acidic alumina (Aldrich Activated Brockmann 1). After mixing for 2 hours at 95° C., the mixing was stopped and the product was filtered and analyzed by gas chromatography. The PO-DEA content was only reduced to 2.2 wt %.

Comparative Example H

Removal with Acidic Alumina at Lower Temperature

Comparative Example G was repeated at 50° C. The PO-DEA content was reduced to 2.2 wt %.

Comparative Example I

Removal with Oleic Acid

To a flask was added 50 g of propoxylated cocoamide-DEA having a propoxylated diethanolamine (PO-DEA) content of about 2.8 wt % and 5.0 g of oleic acid. The mixture was mixing for 1 hour at 100° C. At the completion, the mixture was analyzed by gas chromatography. The PO-DEA content was after the treatment was 2.7 wt %.

Comparative Example J

Removal with Oleic Acid at Lower Temperature

Comparative Example I was repeated at 50° C. The PO-DEA content was reduced to 2.5 wt %.

What is claimed is:

1. A process for the preparation of alkylene oxide-adducted hydrocarbyl amides having less than 2 wt % amine by-products, said process comprising:
    a) reacting a $C_4$-$C_{30}$ fatty acid or fatty acid lower alkyl ester with ammonia or a mono- or di-hydroxy hydrocarbyl amine to form a hydrocarbyl amide;
    b) reacting the hydrocarbyl amide with alkylene oxide; and
    c) extracting the product of b) with water, acidic water, or water-containing inorganic salts or a combination thereof at a temperature from about 5° C. to 95° C. to yield an alkylene oxide-adducted hydrocarbyl amide having less than 2 wt % of amine by-products.

2. The process according to claim 1, wherein the fatty acid is a $C_6$-$C_{24}$ fatty acid.

3. The process according to claim 1, wherein the fatty acid is a $C_6$-$C_{20}$ fatty acid.

4. The process according to claim 3, wherein the fatty acid is coconut oil fatty acid.

5. The process according to claim 1, wherein the lower alkyl group on the fatty acid lower alkyl ester has from about 1 to 6 carbon atoms.

6. The process according to claim 5, wherein the lower alkyl group on the fatty acid lower alkyl ester has from about 1 to 4 carbon atoms.

7. The process according to claim 6, wherein the lower alkyl group on the fatty acid lower alkyl ester has from about 1 to 2 carbon atoms.

8. The process according to claim 7, wherein the lower alkyl ester is a methyl ester.

9. The process according to claim 1, wherein the mono- or di-hydroxy hydrocarbyl amine is selected from the group consisting of ethanolamine, diethanolamine, propanolamine and dipropanolamine.

10. The process according to claim 9, wherein the hydrocarbyl amine is a di-hydroxy hydrocarbyl amine.

11. The process according to claim 10, wherein the di-hydroxy hydrocarbyl amine is diethanolamine.

12. The process according to claim 1, wherein the hydrocarbyl amide is a coconut oil fatty acid amide.

13. The process according to claim 12, wherein the coconut oil fatty acid amide is obtained by the reaction of coconut oil fatty acid or lower alkyl ester and diethanolamine.

14. The process according to claim 1, wherein the alkylene oxide is selected from the group consisting of ethylene oxide, propylene oxide, butylene oxide, pentylene oxide, and mixtures thereof.

15. The process according to claim 14, wherein the alkylene oxide is selected from the group consisting of ethylene oxide, propylene oxide, and a mixture thereof.

16. The process according to claim 15, wherein the alkylene oxide is propylene oxide.

17. The process according to claim 1, wherein the alkylene oxide-adducted hydrocarbyl amide has from about 1 to 30 moles of alkylene oxide per mole of hydrocarbyl amide.

18. The process according to claim 17, wherein the alkylene oxide-adducted hydrocarbyl amide has from about 2 to 20 moles of alkylene oxide per mole of hydrocarbyl amide.

19. The process according to claim 18, wherein the alkylene oxide-adducted hydrocarbyl amide has from about 2 to 10 moles of alkylene oxide per mole of hydrocarbyl amide.

20. The process according to claim 1, wherein the alkylene oxide-adducted hydrocarbyl amide is derived from the reaction of a coconut oil fatty acid amide with ethylene oxide or propylene oxide.

21. The process according to claim 1, wherein the temperature of the extraction of product b) is from about 5° C. to 50° C.

22. The process according to claim 1, wherein the temperature of the extraction of product b) is from about 5° C. to 30° C.

23. The process according to claim 1, wherein the alkylene oxide-adducted hydrocarbyl amide has less than 1.5 wt % amine by-products.

24. The process according to claim 1, wherein the alkylene oxide-adducted hydrocarbyl amide has less than 1.0 wt % amine by-products.

25. The process according to claim 1, wherein the amine by-products may be diethanolamine, alkoxylated diethanolamine or mixtures thereof.

26. The process according to claim 25, wherein the alkoxylated diethanolamine is propoxylated diethanolamine.

\* \* \* \* \*